US006437101B1

(12) United States Patent
Hayenga et al.

(10) Patent No.: US 6,437,101 B1
(45) Date of Patent: Aug. 20, 2002

(54) METHODS FOR PROTEIN PURIFICATION USING AQUEOUS TWO-PHASE EXTRACTION

(75) Inventors: Kirk James Hayenga, Raleigh; Pascal P. Valex, Morrisville, both of NC (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/307,549

(22) Filed: May 7, 1999

(51) Int. Cl.[7] .......................... A61K 38/24; A23J 1/00; C07K 14/00; A01N 43/04

(52) U.S. Cl. ...................... 530/399; 530/402; 530/412; 530/418; 530/419; 530/420; 530/421; 530/427; 514/59; 514/60

(58) Field of Search ................................ 530/399, 402, 530/412, 418, 419, 420, 421, 427; 514/59, 60

(56) References Cited

U.S. PATENT DOCUMENTS

| | | | |
|---|---|---|---|
| 5,139,943 A | * 8/1992 | Heinsohn et al. | 435/226 |
| 5,151,358 A | 9/1992 | Heinsohn et al. | 435/226 |
| 5,328,841 A | * 7/1994 | Lorch et al. | 435/209 |
| 5,407,810 A | 4/1995 | Builder et al. | 435/69.1 |
| 5,695,958 A | 12/1997 | Builder et al. | 435/69.1 |
| 5,723,310 A | 3/1998 | Builder et al. | 435/69.1 |

FOREIGN PATENT DOCUMENTS

| | | |
|---|---|---|
| BE | 857.327 | 1/1978 |
| EP | 0 445 099 | 4/1996 |

OTHER PUBLICATIONS

Grossmann et al., *Biotechnology and Bioengineering*, vol. 60, No. 6, pp. 699–711, Dec. 20, 1998.*
Diamond et al., *Adv. Biochem. Eng. Biotechnol.*, vol. 47, pp. 89–135, 1992.*
Delgado et al., *Critical Reviews in Therapeutic Drug Carrier Systems*, vol. 9, Nos. 3, 4, pp. 294–304, 1992.*
Kohler and Veide, 1994, "Uses of Fusions of β–Galactosidase and Peptides to Proteins", Methods in Enzymology 228:627–640.
Abbott et al., 1990, "On protein partitioning in two–phase aqueous polymer systems," *Bioseparation* 1(3–4):191–225.
Becker and Hsiung, 1986, "Expression, secretion and folding of human growth hormone in *Escherichia coli*. Purification and characterization," *FEBS Lett.* 204(1):145–150.

Diamond and Hsu, 1992, "Aqueous two–phase systems for biomolecule separation," *Adv. Biochem. Eng. Biotechnol.* 47:89–135.
Ettori et al., 1992, "Purification of recombinant human growth hormone by isoelectric focusing in a multicompartment electrolyzer with Immobiline membranes," *J. Biotechnol.* 25(3):307–318.
Jones et al., 1979, "Large–scale preparation of highly purified pyrogen–free human growth hormone for clinical use," *J. Endocrinol.* 82(1):77–86.
Jónsdóttir et al., 1986, "Purification of pituitary and biosynthetic human growth hormone using monoclonal antibody immunoadsorbent," *Mol. Cell. Endocrinol.* 46(2):131–135.
Lefort and Ferrara, 1986, "Hydrophobic adsorbents for the isolation and purification of biosynthetic human growth hormone from crude fermentation mixtures," *J. Chromatogr.* 361:209–216.
Mukhija et al., 1995, "High–level production and one–step purification of biologically active human growth hormone in *Escherichia coli*," *Gene* 165(2):303–306.
Persson et al., 1998, "Purification of recombinant apolipoprotein A–1 $_{Milano}$ expressed in *Escherichia coli* using aqueous two–phase extraction followed by temperature–induced phase separation," *J. of Chromatogr. B* 711(1–2):97–109.
Boris Y. Zaslavsky, *Aqueous Two–Phase Partitioning: Physical Chemistry Bioanalytical Applications* Marcel Dekker, Inc., New York 1995, pp. 221–276.
Delgado et al., 1992, "The Uses and Properties of PEG–Linked Proteins," *Critical Reviews in Therapeutic Drug Carrier Systems* 9(3,4):249–304.
Grossmann et al., 1998, "Partitioning of Low Molecular Combination Peptides in Aqeuous Two–Phase Systems of Poly(ethylene glycol) and Dextran in the Presence of Small Amounts of $K_2HPO_4/KH_2PO_4$ Buffer at 293 K: Experimental Results and Predictions," *Biotechnol. Bioeng.* 60:699–711.

* cited by examiner

*Primary Examiner*—Christopher S. F. Low
*Assistant Examiner*—Abdel A. Mohamed
(74) *Attorney, Agent, or Firm*—William P. Ramey, III

(57) ABSTRACT

Methods are provided in this invention for the isolation of human growth hormone, growth hormone antagonist, or a homologue of either, from a biological source. The methods of the invention use multi-phase extraction.

23 Claims, 5 Drawing Sheets

METHODS FOR PROTEIN PURIFICATION USING AQUEOUS TWO-PHASE EXTRACTION

1. FIELD OF THE INVENTION

Figure 1:
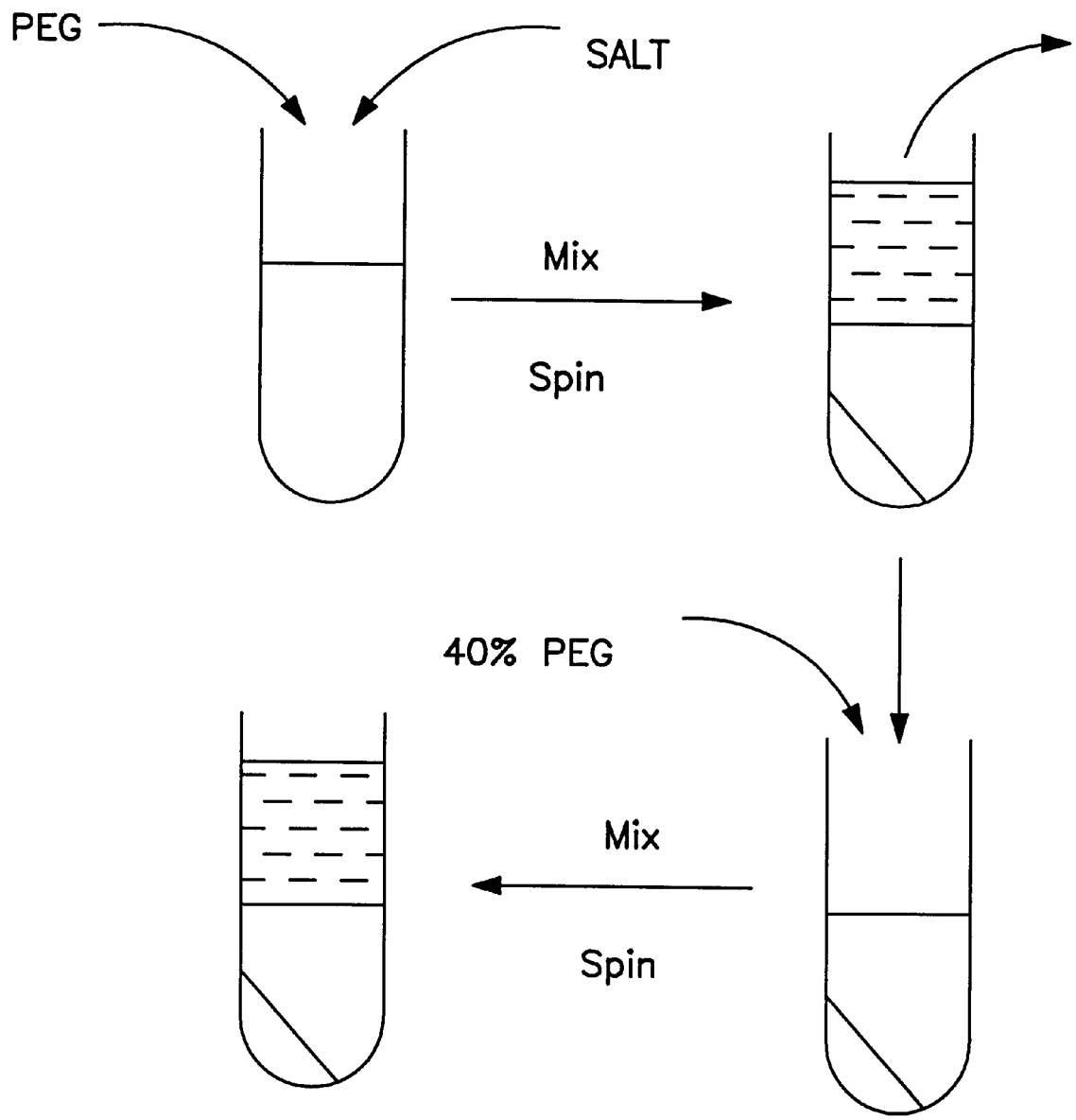

The present invention relates to methods for the purification of proteins using two-phase liquid-liquid extraction procedures. In particular, the methods of the invention are useful for the purification of human growth hormone, human growth hormone antagonists and their homologues.

2. BACKGROUND OF THE INVENTION

Proteins are components of living organisms that play critical roles in phenomena like metabolism, gene expression, signal transduction, cellular and extracellular structures, and the like. Many proteins are useful for therapeutic or diagnostic applications; however, in order to utilize them therapeutically or diagnostically, it is necessary to prepare the protein of interest in pure form, i.e., without contaminants that could jeopardize the therapeutic or diagnostic goals and potentially put a patient's health at risk.

The purification of proteins has long been a challenge, especially when large scale purification is sought as is typically required for therapy or diagnostics for large numbers of patients. However, even when small or medium scale purification of proteins is desired, a procedure that is fast and easy to carry out, while providing the protein of interest in sufficiently pure form and with high yields, is very desirable.

Human growth hormone ("hGH") and antagonists for hGH, i.e., growth hormone antagonists ("GHA"), are examples of proteins that are useful for a variety of therapeutic applications. hGH has been used for the treatment of hypopituitary dwarfism and all conditions resulting from low levels of hGH production, whether such condition is caused by genetic defect, injury or hypophysectomy. hGH has also been shown to improve the recovery of bum victims and other hospitalized patients. GHA, on the other hand, has been used to treat acromegaly, a form of gigantism caused by overproduction of hGH. Other possible medical indications of GHA are the prevention of retinopathy in diabetes patients, and the treatment of cancer patients with tumors overexpressing receptors that bind growth hormone (Clark et al., 1996, WO97/11178).

Even though the amino acid sequence of hGH is highly conserved, GH molecules from common domesticated animals do not work in humans. Only the protein extracted from the glands of higher primates functions in humans. As a consequence, hGH has originally been purified from pituitary glands recovered from cadavers. The general purification method involved extraction from tissues under mild alkaline conditions (Jones et al., 1979, J. Endocrinology 82:77–86) or with hot glacial acetic acid, followed by a series of fractionations by pH, ammonium sulfate, ethanol precipitation or polyethylene glycol precipitation (Nordisk Insulinlab, 1978, BE 857327) and a few chromatographic steps. It has also been purified from crude pituitary extract by immunoaffinity chromatography (Jonsdottir et al., 1986, Mol. Cell. Endocrinol. 46:131–135).

However, pituitary derived hGH has recently been linked to a certain number of cases of Creuzfelds-Jakob and has been removed from the market. To avoid this kind of problem, hGH had to be expressed in different systems. Early on, it was isolated from the supernatant of transformed monkey kidney cell cultures using hydrophobic interaction chromatography (Lefort et al., 1986, J. Chromatogr. 361:209–216). hGH does not undergo glycosylation and may therefore advantageously be expressed as a recombinant product in bacteria. In fact, hGH has been expressed in *Bacillus subtilis* (Franchi et al., 1991, J. Biotechnol. 18:41–54) and in *Eschericia coli*. Several extraction methods have been used, depending on the state of the expressed protein. hGH produced in the form of inclusion bodies was extracted by solubilization in elevated concentrations of chaotropic agents such as guanidine hydrochloride (Mukhija et al., 1995, Gene 165:303–306) or urea. Following refolding, the protein was then separated either by selective pH precipitation (Storrs et al., 1990, EP 445099) or directly loaded onto a chromatography column. hGH expressed in a soluble form has been purified from the periplasmic fraction of *E. coli* by anion exchange (Becker et al., 1986, FEBS Lett. 204:145–150) or from the crude cell lysate by immunoaffinity chromatography (Jonsdottir et al., 1986, supra) and ion exchange chromatography (Ettori et al., 1992, J. Biotechnol. 25:307–318).

Aqueous two-phase partitioning has been employed to separate proteins from cellular debris or to separate proteins from one another. Liquid-liquid extraction relies on the incompatibility between two polymers in aqueous solution, or one polymer and a salt present at high concentration. This incompatibility will result in the formation of two separate phases of very different compositions. The protein molecules will partition preferentially into one phase or the other, depending on their characteristics (Diamond et al., 1992, Advances in Biochem. Eng. Biotechn. 47:89–135).

Aqueous two-phase extraction procedures have been applied to the purification of hGH but such procedures always included chaotropic agents which denatured hGH (Builder et al., U.S. Pat. Nos. 5,407,810; 5,695,958; 5,723,310). However, the use of a chaotropic agent like, for example, urea, guanidine salts or thiocyanate salts to denature the hGH protein has critical disadvantages, especially when using the purification method on a large scale. For example, such chaotropic agents raise the cost of hGH purification, particularly as the chaotropic agent has to be available in a pure form. Also, once the hGH protein is denatured it must be refolded prior to most uses, especially prior to therapeutic uses, thereby increasing the necessary processing steps and potentially decreasing the amount of biologically active proteins.

The partition coefficient of hGH in a two-phase system was used to analyze the purity of hGH preparations following its purification and prior to its therapeutic use. However, no two-phase extraction procedures that do not use a chaotropic agent has been used to purify hGH or GHA (Heinsohn et al, U.S. Pat. Nos. 5,139,943; 5,151,358; Lorch et al., U.S. Pat. No. 5,328,841).

Thus, a simple, rapid and cost-effective method to isolate hGH and GHA using two-phase extraction without the need for a chaotropic agent is highly desirable.

3. SUMMARY OF THE INVENTION

The invention relates to aqueous two-phase extraction methods, wherein no chaotropic agent is used, for the purification of hGH and GHA, and homologues of either. The methods of the current invention are useful for the purification of recombinant hGH and GHA, and homologues of either, from any source.

In one aspect of the current invention, the methods provide for multi-phase extraction for the isolation of hGH, rGHA or a homologue of either. In a preferred embodiment of the current invention, the multi-phase extraction methods provide for two-phase extraction for the isolation of hGH, rGHA or a homologue of either. In another aspect of the current invention, the extraction methods provide for two-stage extraction for the isolation of hGH, RGHA or a homologue of either. Such extraction methods use a phase forming agent such as polyethylene glycol ("PEG"), a dextran, a ficoll, a Ucon or a poly(vinyl methyl ethyl ether), wherein each of the polymers can be used in various molecular weights for the isolation of hGH, rGHA or a homologue of either. In a preferred embodiment, PEG of molecular weights 2000, 4600 or 8000 is used as a phase forming agent. In another embodiment, a phase forming salt useful for the practice of the current invention is ammonium sulfate, sodium carbonate, potassium phosphate, magnesium sulfate or sodium sulfate for the isolation of hGH, rGHA or a homologue of either. In one aspect of the current invention, the extraction methods provided use Tris buffer, phosphate buffer, MES buffer, HEPES buffer or citrate buffer for the isolation of hGH, rGHA or a homologue of either. In one embodiment of the current invention, the extraction methods use as the source of the proteins to be purified any cell, tissue or animal, for example, animal cells, insect cells, plant cells, gram negative bacteria, gram positive bacteria, filamentous fungi, yeast or transgenic animals, or an extract or a supernatant derived from any one of the above. In a preferred embodiment, *Escherichia coli* cells are used. The extraction methods disclosed herein do not use a protein denaturing agent such as a chaotropic agent.

In a specific embodiment by way of examples, the extraction methods of the invention use PEG at concentrations of about 6% to about 15% weight per volume in the extraction mixture for the isolation of hGH, rGHA or a homologue of either. In addition, the extraction methods use ammonium sulfate at concentrations of about 6% to about 15% weight per volume in the extraction mixture for the isolation of hGH, rGHA or a homologue of either. The extraction methods are carried out at a pH of from about 6 to about 8 for the isolation of hGH, rGHA or a homologue of either.

The extraction methods disclosed herein can be carried out at small scale starting with less than about 10 liters of extraction mixture volume for the isolation of hGH, rGHA or a homologue of either. The extraction methods can also be carried out at medium scale of more than about 10 liters and less than about 100 liters of extraction mixture volume for the isolation of hGH, rGHA or a homologue of either. In a preferred embodiment, the extraction methods of the invention are carried out at large scale of more than about 100 liters of extraction mixture volume for the isolation of hGH, rGHA or a homologue of either.

4. BRIEF DESCRIPTION OF THE DRAWINGS

FIG. 1 shows an outline of the extraction methods of the current invention. The extraction procedure as shown begins with the addition of PEG and a salt to the cell lysate (upper left comer) resulting in the extraction mixture. Then, the mixture is thoroughly mixed and centrifuged so that two fluid phases are formed of which the top light phase is enriched in the protein of interest. The top phase is removed (upper right comer). Then, a reextraction step may optionally be carried out by first adding a 40% PEG solution to the remaining lower heavy phase (lower right comer). The amount of the PEG solution added is such that, after mixing and centrifuging the second extraction mixture, an upper light phase is formed that is about equal in volume to the upper light phase formed in the first extraction. The second extraction mixture is then mixed and centrifuged resulting in a second top light phase that is enriched in the protein of interest when compared to the lower heavy phase.

Figure 2A:
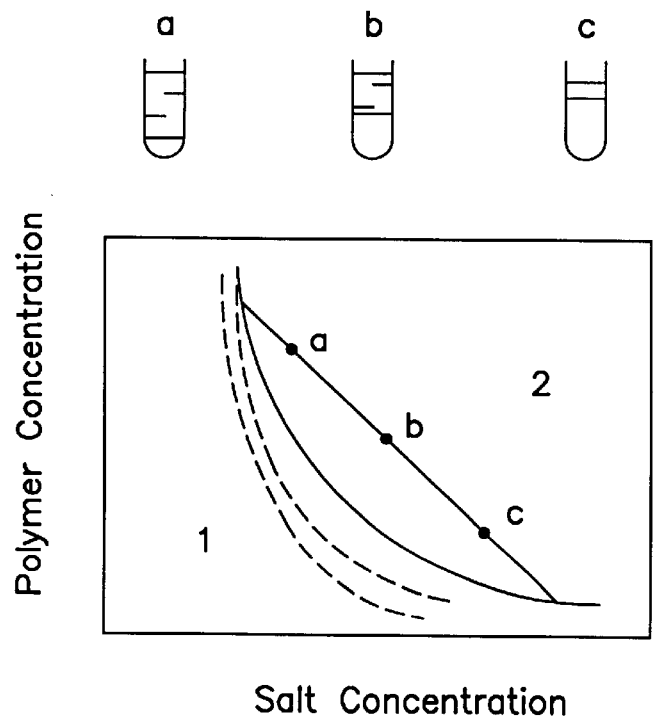
Figure 2B:
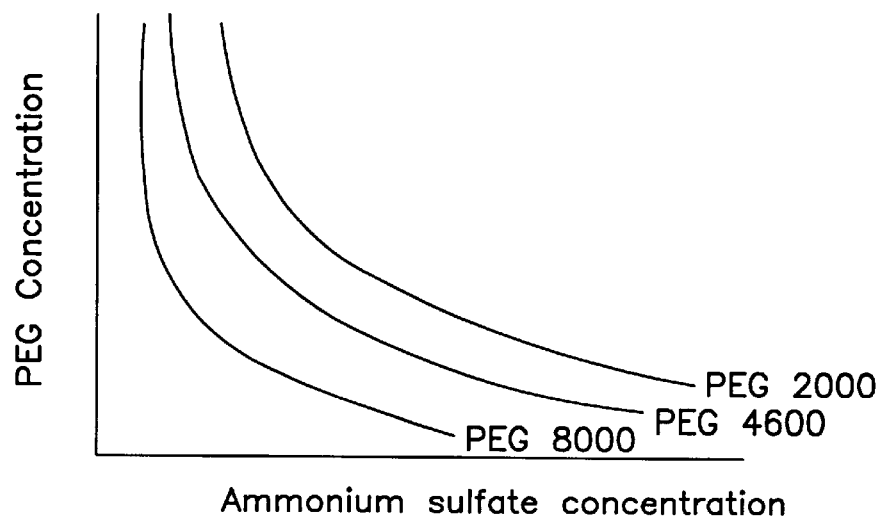

FIG. 2A shows a phase diagram for a mixture of a polymer and a salt. The curved lines, solid and broken, are binodal curves. The binodal curves indicate the set of phase forming agent concentrations at which phase separation occurs. Any point in the domain to the left of the binodal curve represents a monophasic system. Any point to the right of the binodal curve represents a diphasic system. The straight line, going through points a, b and c, is a tie line, i.e., the partition coefficient of the protein stays unchanged as the composition of the mixture is changed along the tie line. All systems on the tie line yield the same two phases, the compositions of which are described by the intersections of the tie line with the binodal curve. The reaction mixes depicted under a, b and c, above the phase diagram, are examples of the phase volumes as the composition of the system is changed along the tie line and the depicted mixes correspond to the points a, b and c along the tie line in the phase diagram. The yield of the extraction procedure will depend on the partition coefficient and the volume of the target phase recovered, i.e., the yield will depend on the tie line and the position of the system on that tie line. FIG. 2B shows how the position of the binodal curve can shift. Several factors influence the position of the binodal curve. In the case of PEG-salt systems, increasing molecular weight of the PEG chains will push the binodal curve towards lower salt concentrations.

Figure 3A:
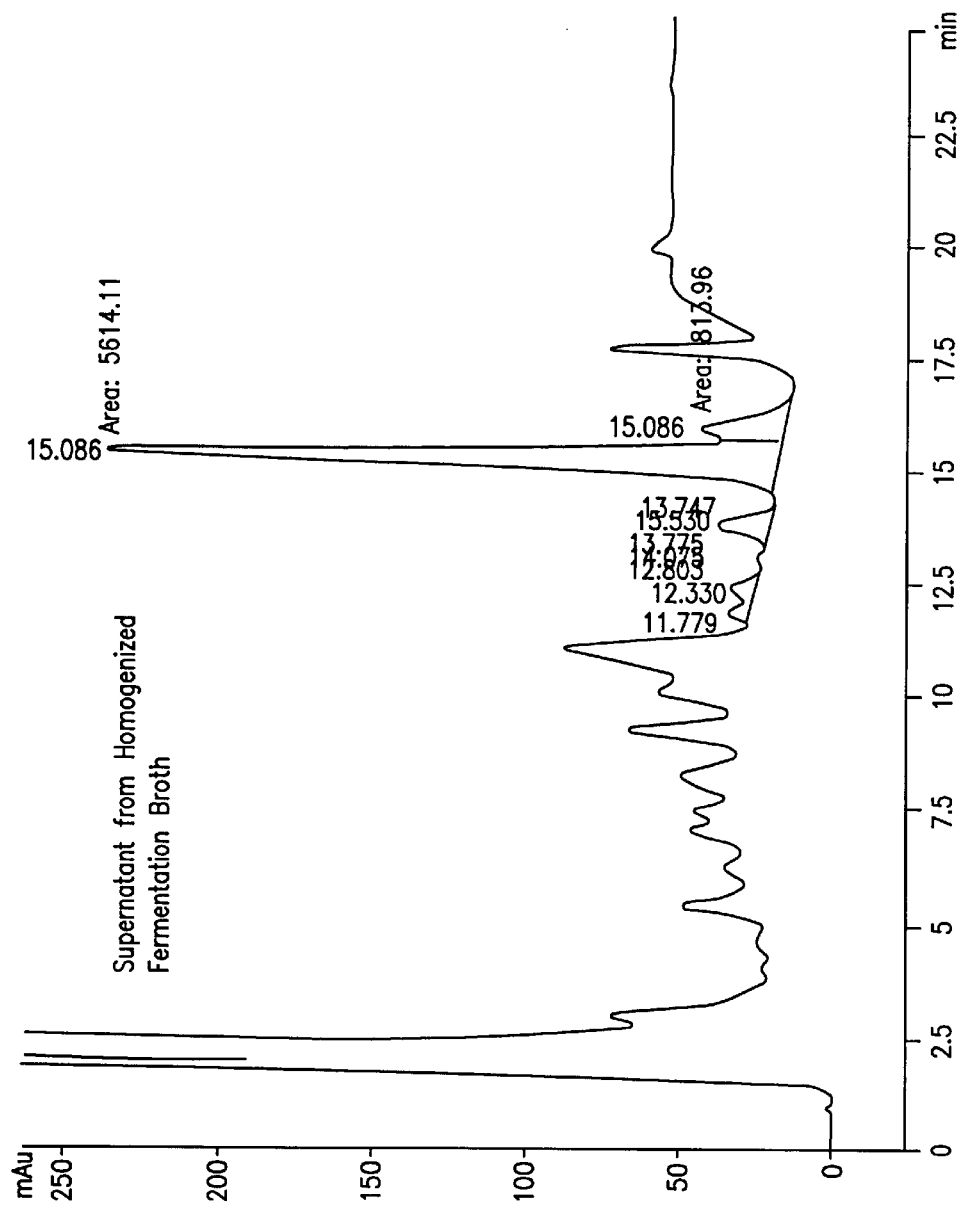
Figure 3B:
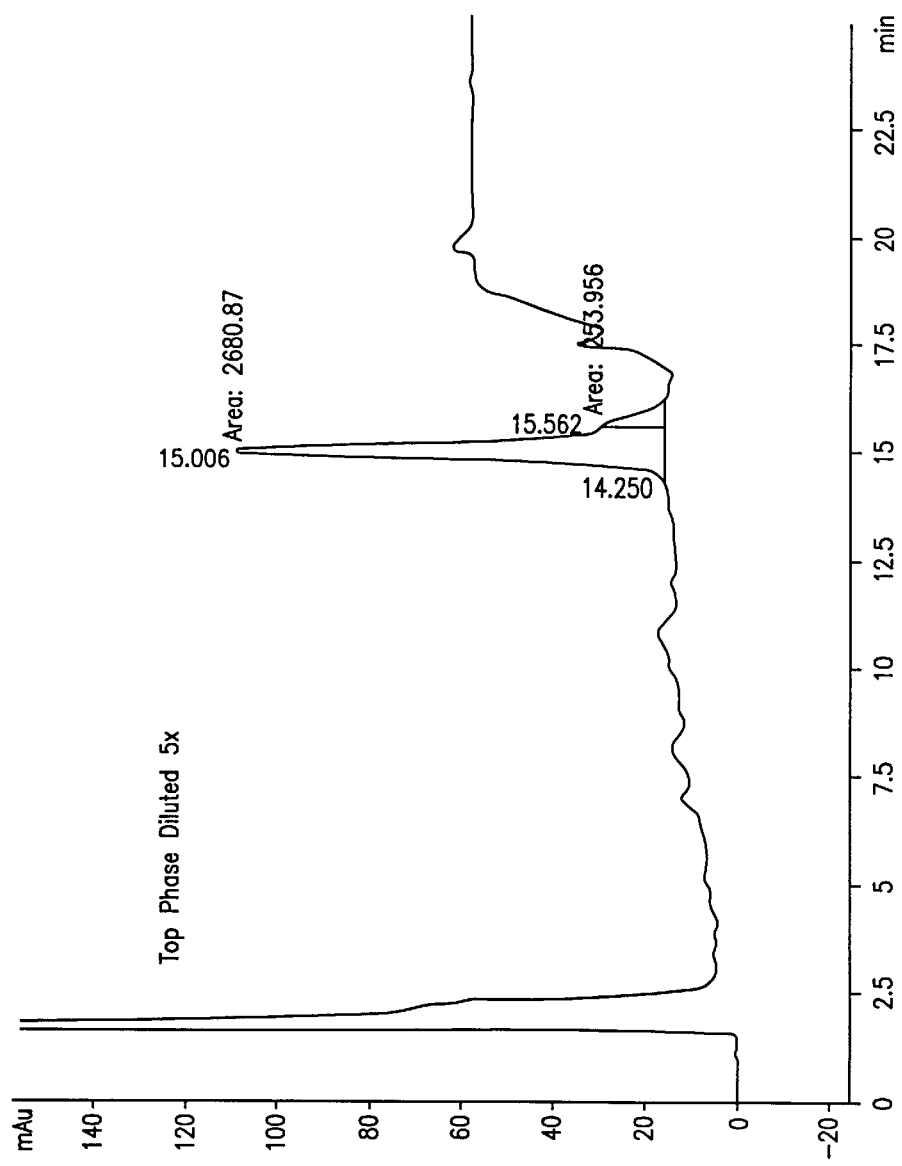
Figure 3C:
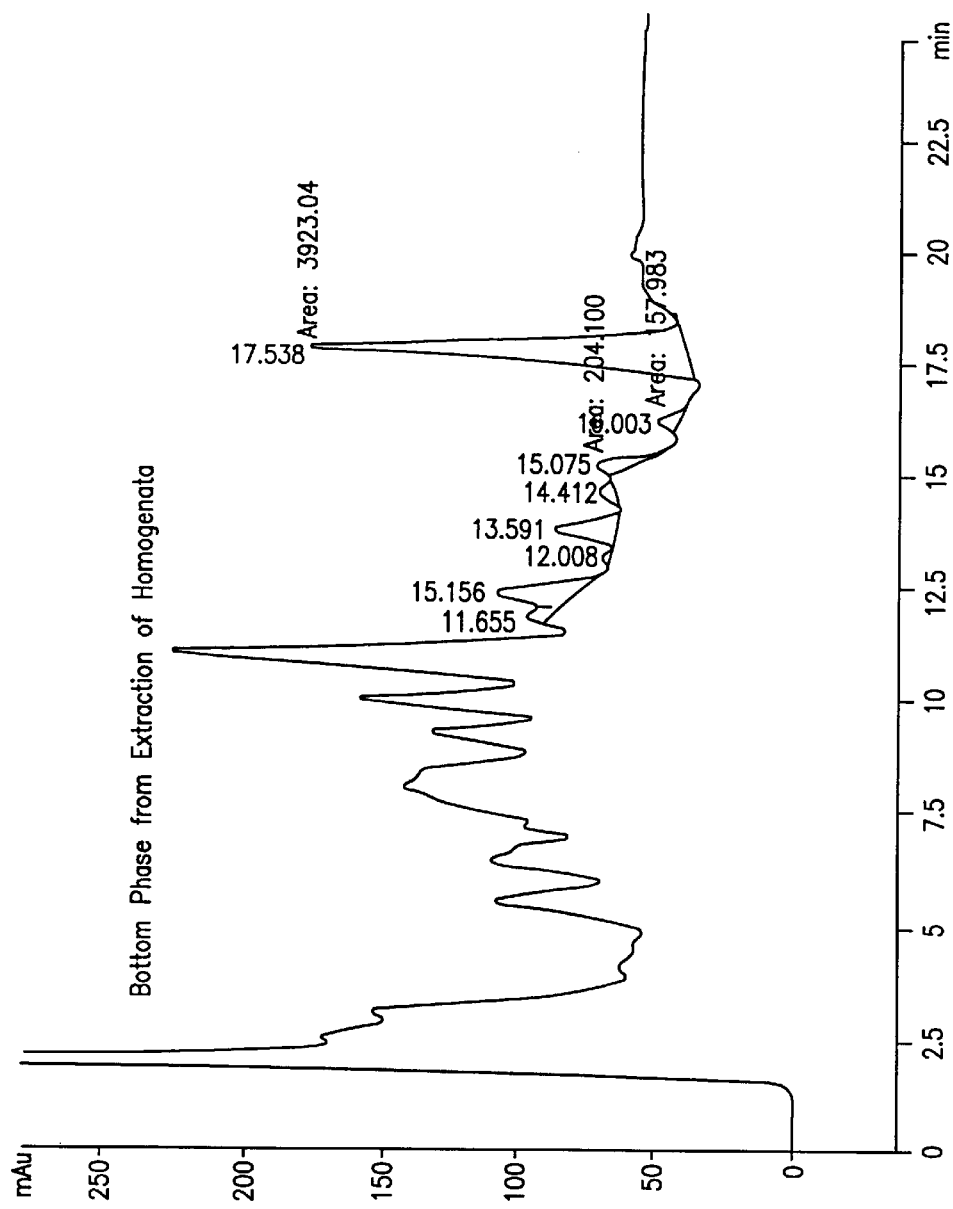

FIGS. 3A–3C show C-4 RP HPLC chromatograms of a cell culture homogenate supernatant (FIG. 3A) and following two-phase extraction using 8% PEG and 10% ammonium sulfate at pH 8.0 (FIGS. 3B and 3C). In the chromatograms presented in FIGS. 3A–3C, the void peak at about 2 minutes was not integrated. The void peak is the material that does not bind the column which is probably very small proteins and fermentation products such as color. FIG. 3A shows a C-4 Reverse phase chromatogram that represents the starting material for the two-phase extraction. This represents homogenized cells in fermentation broth after the solids have been spun out (supernatant from homogenate). GHA can be seen at about 15 minutes. The remaining peaks are contamination proteins. FIG. 3B shows a chromatogram that represents the 5×diluted top phase obtained following two-phase extraction. The yield of 313 ug/ml is actually 5×313 ug/ml or 1.565 mg GHA/ml. GHA elutes at about 15 min. The purity is represented by the chromatogram. FIG. 3C shows a chromatogram that represents the undiluted bottom phase. The concentration is 58.8 ug/ml.

5. DETAILED DESCRIPTION OF THE INVENTION

The present invention relates to methods for the isolation of hGH and related molecules. The details for practicing the invention are described in the subsections below.

5 5.1. hGH and GHA Proteins

The methods of the current invention are useful for the isolation of hGH, rGHA, or a homologue of either (collectively referred to hereinafter as "the protein", unless the context indicates otherwise).

hGH protein sequences and variants thereof have been disclosed in U.S. Pat. Nos. 5,849,535; 5,834,598; 5,597,709; 4,898,830; 4,658,021, all of which are incorporated herein by reference in their entirety. rGHA protein sequences and variants thereof have been disclosed in U.S. Pat. Nos. 5,681,809; 5,350,836, all of which are incorporated herein by reference in their entirety.

The term "homologue", as used herein, refers to a polypeptide that is equivalent to hGH or rGHA. Such equivalent polypeptides are characterized by, for example, additions, deletions or substitutions of amino acid residues within the amino acid sequence of hGH or rGHA which result in a silent change. Such a silent change would result in a polypeptide that is likely to have similar partitioning properties and will therefore be equally susceptible to purification using a method of the current invention. It is preferred that a silent change has no effect on the biological activity of the polypeptide. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Other parameters that define a polypeptide as equivalent to hGH or rGHA with respect to its purification using the methods of the current invention are the overall hydrophobicity or hydrophilicity of the polypeptide, the pKa value of the polypeptide, its size, the arrangement of amino acid domains in the polypeptide, the clustering of certain amino acids into domains, the structure of the polypeptide as characterized by its ability to react with an antibody that can react with either hGH or rGHA, and the like.

For example, the mature human growth hormone is a single polypeptide chain of 191 amino acids with two disulfide bonds when properly folded. It has a molecular weight of about 22 kilodalton and an isoelectric point near 5.3, which is also the pH value at which the polypeptide is the least soluble.

5.1.1. Sources of hGH and GHA Proteins

While hGH and GHA are relatively small proteins that can be chemically synthesized (e.g., see Creighton, 1983, Proteins: Structures and Molecular Principles, W. H. Freeman & Co., N.Y.), they may advantageously be produced by recombinant DNA technology using techniques well known in the art for expressing genes. These methods include, for example, in vitro recombinant DNA techniques, synthetic techniques, and in vivo genetic recombination. See, for example, the techniques described in Sambrook et al., Molecular Cloning, Cold Spring Harbor Laboratory Press, Cold Spring Harbor, N.Y., Vols. 1–3: (1989), and periodic updates thereof, and Ausubel et al., eds., 1989, Current Protocols in Molecular Biology, Green Publishing Associates, Inc., and John Wiley & sons, Inc., New York. DNA and RNA encoding any of the nucleotide sequences described above may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express hGH and GHA. The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing a nucleotide sequence encoding hGH or GHA; yeast (e.g., Saccharomyces, Pichia) transfected with recombinant yeast expression vectors containing a nucleotide sequence encoding hGH or GHA; insect cell systems infected with recombinant virus expression vectors (e.g., baculovirus) containing a nucleotide sequence encoding hGH or GHA; plant cell systems infected with recombinant virus expression vectors (e.g., cauliflower mosaic virus, CaMV; tobacco mosaic virus, TMV) or transfected with recombinant plasmid expression vectors (e.g., Ti plasmid) containing a nucleotide sequence encoding hGH or GHA; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter; the vaccinia virus 7.5K promoter).

In eukaryotic systems, a number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hprt$^-$ or aprt$^-$ cells, respectively. Also, antimetabolite resistance can be used as the basis of selection for the following genes: dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

In bacterial systems, a number of expression vectors may be selected depending upon the use intended for the hGH and GHA protein. The bacteria suitable for the practice of the invention are gram positive and gram negative bacteria. In a preferred embodiment, the protein is expressed in *Eschericia coli* ("*E. coli*") bacteria and subsequently isolated from the cells using a method of the current invention. The protein can be expressed in a procaryotic cell using expression systems known to those of skill in the art of biotechnology. Expression systems useful for the practice of the current invention are described in U.S. Pat. Nos. 5,795, 745; 5,714,346; 5,637,495; 5,496,713; 5,334,531; 4,634, 677; 4,604,359; 4,601,980, all of which are incorporated herein by reference in their entirety.

Procaryotic cells can be grown under a variety of conditions known to the skilled artisan. In one aspect of the current invention, the cells are grown in a medium suitable for growth of such cells, for example, minimal media or complete (i.e., rich) media. The medium used to grow the cells should not contain concentrations of salts or other chemicals, for example, urea, which are so high as to interfere with the partitioning of the protein or polypeptide or with the formation of phases during the extraction methods of the present invention.

hGH or GHA can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate transgenic animals expressing a transgene encoding hGH, GHA or a homologue.

5.2. Aqueous Two-Phase Extraction Purification

The methods of the current invention are useful for the purification of hGH, GHA or a homologue from a crude mixture that may be rich in contaminants like, for example, cell extracts. Cells that express the protein can be prepared prior to the purification procedure in a variety of ways. For example, one may prepare a paste of frozen dead cells, or one may use living cells that are frozen. Or, living cells can be used directly in the extraction procedure.

The methods of the current invention relate to aqueous multi-phase extraction for the purification of hGH and GHA. In a preferred embodiment of the current invention, aqueous two-phase extraction is carried out. If hGH or GHA is purified from cells, the cells are disrupted or homogenized prior to extraction of the protein. The purpose for disrupting or homogenizing the cells is to release hGH or GHA from the cells. A variety of ways to disrupt or homogenize cells of diverse origin are well known in the art, for example, bead mills, osmotic shock, freeze fracture. In a preferred aspect of the invention, the source is disrupted or homogenized by use of a microfluidizer. In another preferred aspect, a high pressure homogenizer (e.g., a Niro) is used. If the protein or polypeptide is secreted from the cells in which it is synthesized, the cells do not have to be lysed but the protein or polypeptide can be extracted from the extracellular fluid or culture medium, e.g., the phase forming agent is added directly to the fermentor.

In accordance with the current invention the protein can be purified from cells, a cell homogenate, disrupted cells, a crude mixture obtained following chemical synthesis of the protein, or any kind of mixture that contains the protein of interest and contaminants such that purification of the protein is desirable. In one aspect of the invention, the protein is purified from a crude mixture by adding reagents which are capable of forming an aqueous multi-phase system, like, for example, a two-phase system. In a preferred embodiment, the extraction mixture is stirred to dissolve the phase forming agents and to thoroughly mix the system. The resulting extraction mixture is processed to form distinct phases, one of which contains an enrichment of the protein. Such processing can be accomplished, for example, by centrifuging the extraction mixture or by letting the mixture sit undisturbed for several hours (settle or coalesce at 1×gravity), or, for example, by temperature-induced phase separation (Persson et al., 1998, J. of Chromatography 711:97–109, which is incorporated herein by reference in its entirety). In a further aspect, once distinct phases have been formed, the phase that contains an enrichment of the protein, i e., typically the upper light phase, may be removed.

In another embodiment of the current invention, after removal of the phase that contains the protein, the phase that does not contain the protein in enriched form is reextracted ("two-stage extraction"). Reextraction can be performed by adding a solution containing a phase forming agent capable of forming a second light phase so that it will form a phase in the reextraction that is enriched in the protein. In another aspect, during two-stage extraction, the extraction mixture is stirred to dissolve the phase forming agents and to thoroughly mix the system. The resulting reextraction mixture is processed to form distinct phases of which one contains the enriched protein. Such processing can be accomplished, for example, by centrifuging the reextraction mixture or, for example, by temperature-induced phase separation (Persson et al., supra), or by allowing the phases to coalesce under 1×gravity.

In a preferred embodiment, the phase forming reagents are added directly to crude mix that contains the protein. Said phase forming reagents are capable of forming a multi-phase system characterized by a result that the protein is enriched in one phase of the multi-phase system whereas the majority of the remaining components of the crude mix do not accumulate in said one phase. More preferably, the multi-phase system is characterized by a result that the protein is enriched in one phase of the multi-phase system whereas substantially all of the remaining components of the crude mix are in the other phases.

5.2.1. Phase Forming Agents Useful for Aqueous Two-Phase Extraction Purification A variety of reagents capable of forming a multi-phase system and preferably a two-phase system can be used. In a preferred embodiment of the current invention, two polymers can be used as phase forming agents to create two phases. More preferably, the two polymers are incompatible with one another in an aqueous solution and therefore lead to the formation of a two-phase system. In another preferred embodiment of the current invention, a polymer and a salt are used as two phase forming agents. More preferably, the polymer and the salt are used under such conditions and at such concentrations so that a two-phase system is created.

Examples of phase forming agents, combinations of phase forming agents and parameters to consider in selecting suitable phase forming agents are discussed in Diamond et al., 1992, supra, and Abbott et al., 1990, Bioseparation 1:191–225, both of which are incorporated herein by reference in their entirety.

In a preferred embodiment of the current invention, a phase forming polymer useful for the practice of the current invention includes but is not limited to a PEG, a dextran, a modified starch, a ficoll, a Ucon or a poly(vinyl methyl ethyl ether), wherein each of the polymers can be used in various molecular weights. PEG of a molecular weight of, for example, 2000, 4600 or 8000 may be used as a phase forming agent. In addition, a phase forming salt useful for the practice of the current invention includes, but is not limited to, ammonium sulfate, sodium carbonate, potassium phosphate, magnesium sulfate or sodium sulfate.

For the practice of the current invention, the concentration of the phase forming agents may be varied. The concentration of agents is provided throughout in weight of the agent per volume of the total multi-phase (or two-phase) solution, unless indicated otherwise. In one aspect, the concentration of the phase forming polymer is from about 4% to about 18%, more preferably from about 6% to about 15%, more preferably from about 8% to about 13%, and most preferably from about 10% to about 12%. In another aspect, the concentration of the phase forming salt is from about 4% to about 18%, more preferably from about 6% to about 15%, more preferably from about 8% to about 13%, and most preferably from about 10% to about 12%.

In yet another embodiment of the current invention, a buffer is added to the extraction mixture containing, for example, a cell lysate and the phase forming agents, for example, a Tris buffer, a phosphate buffer, a MES buffer, a HEPES buffer or a citrate buffer. In a preferred embodiment, a Tris buffer is used. The pH of the buffer solution is generally from about 5 to about 9, more preferably from about 6 to about 8, more preferably from about 6.5 to about 7.5 and most preferably about 7.

In another embodiment, a salt may be added to the extraction mixture, for example, a salt of a monovalent cation, e.g., sodium, potassium, lithium or caesium, or a bivalent cation, e.g., magnesium, calcium. The anion of the salt may be monovalent, e.g., chloride, nitrate, iodide, thiocyanate. In a preferred aspect, the salt is sodium chloride. The concentration of the salt in the extraction mixture is from about 10 mM to about 1000 mM, preferably from about 30 mM to about 700 mM, preferably from about 50 mM to about 400 mM, preferably about 70 mM to about 200 mM, and most preferably about 100 mM. The salt may be added to the extraction mixture at any point during the procedure, e.g., before adding the phase forming agents, after adding one or more than one phase forming agent, or as part of the buffer solution. For background on the use of a salt additive in two-phase extraction purification, see, e.g., Boris Y. Zaslavsky, Aqueous Two-Phase Partitioning: Physical Chemistry and Bioanalytical Applications (Marcel Dekker, Inc., New York 1995). Centrifugation for the formation of the phases is generally carried out at temperatures from about 10 degrees Celsius ("° C.") to about 40° C., more preferably at from about 15° C. to about 35° C., more preferably at from about 20° C. to about 30° C., and most preferably at about 25° C.

The extraction methods of the current invention are generally carried out with a starting extraction mixture volume of less than about 10 liters. In another embodiment, the extraction mixture volume is more than about 10 liters and less than about 100 liters. In yet another embodiment, the extraction mixture volume is more than about 100 liters.

The yields obtained, after two-phase extraction, when purifying a protein or polypeptide using the method of the present invention can be expressed in grams per one thousand liters of cell culture. For example, when purifying a protein from a culture of E. coli using the methods of the invention, the yield per one thousand liters of cell culture is at least about 100 g, preferably at least about 200 g, more preferably at least about 300 g, more preferably at least about 400 g, more preferably at least about 500 g, more preferably at least about 600 g, and most preferably at least about 700 g.

5.3. Detection and Purity of the Protein Following Aqueous Two-Phase Extraction Purification Following extraction purification, the protein can be detected in the phase removed from the extraction system. For example, the protein can be detected by a variety of methods including, but not limited to, bio assays, HPLC, amino acid determination or immunological assays, e.g., radioimmunoassay, ELISA, Western blot using antibody binding, SDS-PAGE. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, and epitope-binding fragments of any of the above.

The amount of the purified protein and their level of purity can be determined by methods well known in the art. For example, and not by way of limitation, one may examine a protein formulation that was prepared using the method of the present invention with polyacrylamide gel electrophoresis followed by staining the gel to visualize the total protein in the gel. In a preferred embodiment, the yield and purity of the protein following two-phase extraction are determined using reverse phase HPLC.

The purity of a formulation of a protein or polypeptide prepared using the method of the present invention may vary depending on the starting material. For example, when purifying a protein that is expressed in E. coli, the resulting preparation contains at least about 40% by weight of the protein or polypeptide of interest, more preferably at least about 50%, more preferably at least about 60%, more preferably at least about 70% and most preferably at least about 80%.

5.4. Processing of the Protein Following Aqueous Two-Phase Extraction Purification The protein or polypeptide preparation obtained using the method of the present invention can be further processed, for example, in order to provide the protein or polypeptide at a higher level of purity. Such higher purity may be required depending on the use for which the protein or polypeptide is intended. For example, therapeutic uses of the protein will typically require further purification following the extraction methods of the invention.

All protein purification methods known to the skilled artisan may be used for further purification. Such techniques have been extensively described in Berger and Kimmel, Guide to Molecular Cloning Techniques, Methods in Enzymology, Volume 152, Academic Press, San Diego, Calif. (1987); Molecular Cloning: A Laboratory Manual, 2d ed., Sambrook, J., Fritsch, E. F., and Maniatis, T. (1989); Current Protocols in Molecular Biology, John Wiley & Sons, all Viols., 1989, and periodic updates thereof); New Protein Techniques: Methods in Molecular Biology, Walker, J. M., ed., Humana Press, Clifton, N.J., 1988; and Protein Purification: Principles and Practice, 3rd. Ed., Scopes, R. K., Springer-Verlag, New York, N.Y., 1987. In general, techniques including, but not limited to, ammonium sulfate precipitation, centrifugation, ion exchange, gel filtration, reverse-phase chromatography (and the HPLC or FPLC forms thereof), and hydrophobic interaction chromatography may be used to further purify the protein.

The following examples are provided to further illustrate the current invention but are not provided to in any way limit the scope of the current invention.

6. EXAMPLE

Purification of Recombinant Growth Hormone and Growth Hormone Antagonist by Aqueous TWO-Phase Extraction

6.1. Materials and Methods

Phase forming agents included polyethylene glycol ("PEG"), a salt and a buffer. The concentration of agents is provided throughout in weight of the agent per weight of the total multi-phase (or two-phase) solution, unless indicated otherwise. PEG was obtained from Aldrich (PEG 2000 and PEG 8000) or Union Carbide (PEG 4600, Sentri grade). Tris buffer and ammonium sulfate were obtained from J. T. Baker (Phillipsburg, N.J.). HPLC was performed on a Hewlett Packard 1090 chromatographic system. Homogenization of cell cultures was carried out with a Microfluidics M110Y or M-210EH microfluidizer or an Alfa-Laval Niro homogenizer.

6.1.1. General Extraction Procedure

Unless otherwise stated in the examples below, *Escherichia coli* cells were lysed using high pressure homogenization of the cells directly from the culture broth (which contained EDTA) or after centrifugation. Following centrifugation, the cells were frozen and stored at minus 20°C. or minus 70° C. The frozen cell pellet was resuspended and homogenized. The cell lysate was placed in a stirred tank and phase forming agents were added to yield the desired final system (FIG. 1).

As an example of the above procedure, a 10% ammonium sulfate and 10% PEG 4600 system would be obtained by adding to 7 liters of lysate, in any order, 1 liter of 1M Tris buffer, pH 7.4, 1 kg of ammonium sulfate and 1 kg of PEG. The mixture was stirred until all agents were dissolved followed by centrifugation to separate the phases. GHA and the contaminant profile of the resulting phases is determined by SDS-PAGE analysis and reverse-phase HPLC. The heavy, salt-rich, phase can be reextracted by adding a PEG solution and by repeating the steps of stirring and of centrifugation. The PEG solution added for reextraction may have a concentration of 30% to 40% PEG, see, FIG. 1.

Different parameters were found to influence the operability and the yield of the extraction procedure. Among these parameter are the type and concentration of PEG, the type and concentration of salt, the pH of the system, the presence of culture media components, and bacterial debris.

The yield of the procedure can be maximized by adjusting a number of the aforementioned parameters. First, the phase volumetric ratio, i.e., the volume of the phases relative to one another, can be varied without changing the partition coefficient of the protein. As shown in FIG. 2, the PEG and salt concentrations can be adjusted along the tie line without changing the partition coefficient of the protein in either the salt rich phase or the PEG rich phase. Thus, by bringing the system closer to point a, see FIG. 2, one can increase the yield of the protein. Second, one can adjust the concentrations of PEG and salt to move to another tie line on which the protein will have a different partition coefficient for the phases. Third, after the initial extraction and after removal of the PEG-rich phase, one can reextract the phase that is rich in cell debris by adding a PEG solution in water or buffer at a concentration of 30–40% followed by stirring, centrifugation and removal of the PEG-rich phase as done in the first extraction.

It was found that phase separation in a two-phase system comprising PEG and ammonium sulfate was sensitive to the temperature during the centrifugation step in which the phases were expected to form. While phases were rarely formed by centrifugation around 4° C., separation of phases readily occurred at temperatures in the range from about 20° C. to about 30° C.

When isolating rGHA using the described extraction procedures, it was found that rGHA precipitated when kept in the PEG-rich phase. This problem was avoided by diluting the phase with water after its removal from the remainder of the extraction system. Dilution factors of up to 5-fold were found useful and effective in preventing rGHA precipitation.

When isolating rGHA or hGH, it was important to avoid foaming as both proteins seemed sensitive to liquid-air interfaces.

6.2. Extraction of rGHA Using Different Conditions

Purified human recombinant GHA was isolated using the two-phase extraction method with different agents at different pH values. Phase forming agents used were PEG, ammonium sulfate and Tris buffer. PEG was used in three different molecular weights, i. e., 2000, 4600 and 8000 Daltons. For each of these molecular weight versions, the concentration of PEG in the extraction mixture was 15%. Ammonium sulfate was used at a concentration of 15% in the extraction mixture. Tris buffer was prepared as a 1 M solution and used at a concentration of 100 mM in the extraction mixture. The pH value for the Tris buffer used was 6.0 or 8.0.

After the phase forming agents were added to the purified GHA solution, the resulting mixture was stirred and then centrifuged in a microfuge at a speed of 14000 rpm for 5 minutes at room temperature. Following the centrifugation step, the PEG-rich upper phase was removed and the phases were analyzed by reverse phase HPLC. The results are shown in Table 1.

TABLE 1

Recombinant GHA partitioning in two-phase systems with 15% PEG and 15% ammonium sulfate

| PEG | pH | Phase vol. top$_{(ml)}$ | Phase vol. bottom$_{(ml)}$ | rGHA conc. top$_{(mg/ml)}$ | rGHA conc. bottom$_{(mg/ml)}$ |
|---|---|---|---|---|---|
| 2000 | 8.0 | 0.35 | 0.5 | 0.643 | LOD[1] |
| 2000 | 6.0 | 0.35 | 0.5 | 0.634 | LOD[1] |
| 4600 | 8.0 | 0.25 | 0.6 | 0.675 | LOD[1] |
| 4600 | 6.0 | 0.25 | 0.6 | 0.673 | LOD[1] |
| 8000 | 8.0 | 0.25 | 0.6 | 0.570 | LOD[1] |
| 8000 | 6.0 | 0.30 | 0.5 | 0.557 | LOD[1] |

[1]LOD: Limit of detection, i.e., no rGHA was detected using the means described.

The results presented in Table 1 show that the extraction was approximately equally efficient at pH 6 and 8. Among the various PEG forms examined, the best results were obtained with PEG of molecular weight 4600 Dalton.

6.3. Partition Characteristics of hGH

The partition coefficient of hGH in a two-phase system using PEG and ammonium sulfate was determined. The composition of the mixture was 10% PEG 4600, 10% ammonium sulfate and 100 mM Tris buffer of pH 7.2. In some assays,-the system also included 100 mM NaCl. Lyophilyzed hGH was dissolved in water at a concentration of 5 mg/ml.

An extraction experiment was carried out by mixing in an Eppendorf tube 20 uL of the hGH stock solution, 380 uL of water, 100 uL of 1 M Tris buffer at pH 7.2, 250 uL of a 40% PEG 4600 solution and 250 uL of a 40% ammonium sulfate solution. After thorough mixing, the solution was centrifuged in a microfuge at 14000 rpm or 13000×g. The concentration of hGH in the top and bottom phases was then determined by reverse phase HPLC.

TABLE 2

Human GH partitioning in a two-phase system with 10% PEG and 1% ammonium sulfate

| Buffer used*: | Run #: | Top phase: hGH (mg/l) | Top phase: volume (ul) | Bottom phase: hGH (mg/l) | Bottom phase: volume (ul) | Partition coefficient |
|---|---|---|---|---|---|---|
| Tris, HCl | 1 | 233.1 | 350 | 13.11 | 600 | 10.37 |
| Tris, HCl | 2 | 235.8 | 400 | 8.06 | 600 | 19.5 |
| Tris | 1 | 231.1 | 400 | 8.57 | 600 | 17.9 |
| Tris | 2 | 243.7 | 400 | 6.59 | 600 | 24.6 |
| Tris, NaCl | 1 | 243.9 | 400 | 5.81 | 600 | 28.0 |
| Tris, NaCl | 2 | 258.6 | 400 | 5.61 | 600 | 30.7 |

*Tris, HCl: 1M TRIS-HCl, pH 7.2
Tris: 1M TRIS-base, pH 7.2
Tris, NaCl: 1M TRIS-base, 100 mM NaCl, pH 7.2

The results presented in Table 2 show that hGH preferably partitioned into the PEG rich phase of the extraction system.

6.4. Extraction of rGHA from Heat Killed Frozen Cell Paste

Heat killed frozen *E. Coli* cell paste was suspended in 10 volumes of 0.02 M Tris buffer at pH 7.65 containing 5 mM EDTA, e.g., 10 mL of buffer were used to suspend 1 g of frozen cell paste. The cells were lysed by single-pass homogenization at 13,000 to 15,000 psi leading to the rupture of over 95% of the cells as determined by inspection of the lysate with a microscope. PEG of molecular weight 4600 and ammonium sulfate were added to a final concentration of 15% each, followed by thorough mixing and, finally, centrifugation at 5000 rpm, or 7280×g for 30 minutes at 25° C. Although the above procedure performed better than if PEG of molecular weights 2000 or 8000 was used, it was found that cell debris did not sediment effectively and that phases separated poorly.

To improve the purification of the protein, a lower concentration of PEG or ammonium sulfate or both was substituted in the above protocol. The concentrations that were most useful for extraction of rGHA were 6–10% of PEG and 10–12% of ammonium sulfate.

Following centrifugation in the above extraction procedure, two liquid and two solid phases appeared of which the top clear phase contained an enrichment in rGHA. SDS-PAGE analysis showed that a significant quantity of rGHA sedimented with the cell debris in the bottom phase.

6.5. Extraction of rGHA from Live Frozen Cells

Live frozen *E. coli* cells were prepared by centrifuging cultured cells at 5000 rpm, 7280×g for 30 minutes at 4° C. and transferring the cell pellet into a sealable bag for freezing at minus 70° C. The extraction procedure was carried out as described in Section 6.4., supra. The results are summarized in Tables 3 and 4. All data shown in Tables 3 and 4 were obtained with a single extraction, i.e., without a second or further extraction of the heavy cell debris rich phase.

reverse phase analysis of the light phase rich in rGHA and the heavy phase rich in cell debris. The results typical of such extractions are presented in FIGS. 3A–3C.

6.6. Extraction of rGHA from Live Cells

Cultured *E. coli* cells were harvested, pooled and lysed by single-pass microfluidization at 14,000 psi. The resulting cell lysate was used in the extraction procedure by adding to 21 liters of lysate 3 liters of 1 M Tris buffer at pH7.2, 3 kg of ammonium sulfate and 3 kg of PEG 4600. The resulting mixture was thoroughly mixed and then centrifuged at 5000 rpm for 30 minutes at 25° C. The top phase was recovered and the bottom phase was reextracted with 6 liters of a 40% solution of PEG 4600 in water. Following mixing and centrifuging as for the first extraction, the second top phase was removed and pooled with the first top phase. The yield in rGHA protein was 22.3 g or 1.06 g of rGHA per liter of starting cell culture.

TABLE 3

Recombinant GHA recovery from live frozen cells using two-phase extraction

| Scale (total weight of system) | PEG 4600 (%) | Amm. sulfate (%) | rGHA light phase (ug/ml) | Total rGHA light phase (mg) | rGHA heavy phase (ug/ml) | Total rGHA heavy phase (mg) |
|---|---|---|---|---|---|---|
| 30 g | 6 | 12 | 2291 | 11.4–13.7 | 227 | 4.5–5.7 |
| 30 g | 10 | 10 | 1608 | 16.1 | 196 | 3.5 |
| 30 g | 8 | 10 | 1697 | 15.2 | 275 | 5.5 |
| 15 g | 10 | 10 | 1736 | 7.81 | 171 | 1.54 |
| 15 g | 8 | 10 | 1726 | 6.9 | 254 | 2.41 |

TABLE 4

Partition coefficient of recombinant GHA in two-phase extraction from live frozen cells

| Scale (total weight of system) | PEG 4600 (%) | Amm. sulfate (%) | % Soluble rGHA in light phase | % Soluble rGHA in heavy phase | Partition coefficient |
|---|---|---|---|---|---|
| 30 g | 6 | 12 | 67–75.3 | 24.7–33 | 10.1 |
| 30 g | 10 | 10 | 82 | 18 | 8.2 |
| 30 g | 8 | 10 | 73 | 27 | 6.1 |
| 15 g | 10 | 10 | 83 | 17 | 10.1 |
| 15 g | 8 | 10 | 74 | 26 | 6.8 |

The yield of the above procedure was increased through a second extraction of the heavy phase that is rich in cell debris. Two-stage extraction was carried out by executing a first extraction with 8% PEG 4600 and 10% ammonium sulfate. The scale on which the experiments were carried out, i.e., the total weight of the system, were 30 g for the first extraction and 15 g for the second extraction. Reextraction was carried out by adding a 40% PEG solution in water to the heavy phase after the light phase of the first extraction had been removed. Then, the mixture was stirred and centrifuged at 5000 rpm, 7280×g for 30 minutes at 25° C. Table 5 presents the results of the two stage extraction procedure described above. The procedure was performed with crude homogenate directly after homogenization and with the supernatant of the homogenate after centrifugation.

6.7. Extraction Purification Using Medium Scale Continuous Centrifugation

An Alfa Laval LAPX 202 continuous disk stack centrifuge was used to apply two-phase extraction on a medium

TABLE 5

Two-stage extraction of recombinant GHA from live frozen cells using two-phase extraction

| Experiment | Top phase 1: rGHA (ug/ml) | Top phase 1: total rGHA (mg) | Top phase 2: rGHA (ug/ml) | Top phase 2: total rGHA (mg) | Bottom phase: rGHA (ug/ml) | Bottom phase: total rGHA (mg) | % Total rGHA | % Total rGHA | % Total rGHA |
|---|---|---|---|---|---|---|---|---|---|
| Crude lysate | 1717 | 15.4 | 680 | 7.14 | 155 | 2.79 | 61 | 28 | 11 |
| Lysate supernatant | 1306.5 | 5.88 | 687 | 3.43 | 171 | 1.2 | 56 | 33 | 11 |

The yields of recombinant GHA using the two-stage two-phase extraction procedure were up to about 4.6 mg of rGHA per gram of live frozen cell paste. Recombinant GHA preparations obtained with the two-stage two-phase extraction procedure were examined for purity through HPLC scale. The centriftige was modified as a purifier with one feed, two liquid effluents and axial solids ejection. The centrifuge was fed with a variable speed peristaltic pump. The optimal feed rate was around 450 ml/minute when using a 52 mm gravity ring. A discharge interval of 15 to 20 minutes was determined to be sufficient. Following centrifugation at 10000 rpm or 8200×g, the top phase recovered with the LAPX 202 contained less than 5% of bottom phase contaminants. A two-stage extraction was carried out by reextracting the bottom phase with a volume half that of the bottom phase using a 33% solution of PEG 4600.

The yield from 20 liters of culture was 25.2 g of rGHA or 1.26 g/L of culture. 21.7 g or 86.3% of the protein was recovered during the first extraction and the remaining 3.4 g or 13.7% were obtained during the second extraction.

6.8. Extraction Purification Using High Scale Continuous Centrifugation

An Alfa Laval BPTX 205 disk stack centrifuge equipped with a purifier conversion kit was used to perform two-phase extraction on a large scale, i. e., an about 10-fold scale-up compared to the medium scale procedure. The appropriate feed rate was determined to be about 3–5 L/minute. Large scale extraction was carried out by homogenization of the fermentation broth or suspended cells using the Niro homogenizer at 13,000 to 15,000 psi, followed by adding to 700 liters of lysate, in the order listed, 100 liters of 1 M Tris buffer at pH 7.2, 100 kg of ammonium sulfate and 100 kg of PEG 4600. The solution was mixed thoroughly and centrifuged at 9600 rpm or 12700×g. The protein was recovered from the PEG-rich phase.

The yield in a single-stage extraction, i.e., without executing a reextraction, was about 700 g to about 1000 g of rGHA per 1500 L of fermentation broth.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for purifying a polypeptide selected from the group consisting of human growth hormone, human growth hormone antagonist, homologues of human growth hormone and homologues of human growth hormone antagonist, comprising:

(a) adding a first and a second phase forming agent to a sample containing the polypeptide to form a mixture wherein said first and second phase forming agents may be added in any order;

(b) mixing the mixture of step (a); and (c) separating the mixture of step (b) into two phases;

wherein no chaotropic agent is present in the mixture of step (a) or the mixture of step (b).

2. The method of claim 1, wherein the two phases are separated from each other.

3. The method of claim 1, wherein the polypeptide is human growth hormone.

4. The method of claim 1, wherein the polypeptide is human growth hormone antagonist.

5. The method of claim 1 wherein said first phase forming agent is a salt.

6. The method of claim 5 wherein said salt is selected from the group consisting of ammonium sulfate, sodium carbonate, potassium phosphate, magnesium sulfate and sodium sulfate.

7. The method of claim 1 wherein said second phase forming agent is a polymer.

8. The method of claim 7 wherein said polymer is selected from the group consisting of polyethylene glycol, dextrant, modified starch, ficoll, an ethylene oxide-propylene oxide random co-polymer and poly(vinyl methyl ethyl ether).

9. The method of claim 1 wherein said first and second phase forming agents are polymers.

10. The method of claim 9 wherein each of said first and second phase forming agents is selected from the group consisting of polyethylene glycol, dextran, modified starch, ficoll, an ethylene oxide-propylene oxide random co-polymer and poly(vinyl methyl ethyl ether); and wherein said first and second phase forming agents form a two-phase system.

11. The method of claim 1 wherein said first phase forming agent is ammonium sulfate and said second phase forming agent is polyethylene glycol.

12. The method of claim 11 wherein the concentration of said ammonium sulfate is about 4% to about 18% (w/v) of the sample and wherein the concentration of said polyethylene glycol is about 4% to about 18% (w/v) of the sample.

13. The method of claim 12 further comprising using a buffer.

14. A method for purifying a polypeptide selected from the group consisting of human growth hormone, growth hormone antagonist, homologues of human growth hormone and homologues of growth hormone antagonist comprising:

(a) disrupting cells which contain the polypeptide to provide a sample;

(b) adding a first and a second phase forming agent to the sample to form a mixture, wherein said first and second phase forming agents may be added in any order;

(c) mixing the mixture of step (b); and (d) separating the mixture of step (c) to form two phases;

wherein no chaotropic agent is present in the mixture of step (b) or the mixture of step (c).

15. The method of claim 14 wherein said first phase forming agent is a salt.

16. The method of claim 14 wherein said second phase forming agent is a polymer.

17. The method of claim 14 wherein said first and second phase forming agents are polymers.

18. The method of claim 14, wherein the two phases are separated from each other.

19. The method of claim 14, wherein the polypeptide is human growth hormone.

20. The method of claim 14, wherein the polypeptide is human growth hormone antagonist.

21. The method of claim 14 wherein said first phase forming agent is ammonium sulfate and said second phase forming agent is polyethylene glycol.

22. The method of claim 21 wherein the concentration of said ammonium sulfate is about 4% to about 18% (w/v) of the sample and wherein the concentration of said polyethylene glycol is about 4% to about 18% (w/v) of the sample.

23. The method of claim 22 further comprising using a buffer.

* * * * *

UNITED STATES PATENT AND TRADEMARK OFFICE
CERTIFICATE OF CORRECTION

PATENT NO. : 6,437,101 B1
DATED : August 20, 2002
INVENTOR(S) : Kirk James Hayenga and Pascal P. Valax It is certified that error appears in the above-identified patent and that said Letters Patent is hereby corrected as shown below:

<u>Title page,</u>
Item [75], the spelling of the second inventor's name should read -- Pascal P. Valax --

Signed and Sealed this

Eleventh Day of February, 2003

JAMES E. ROGAN
*Director of the United States Patent and Trademark Office*